United States Patent
Wartini et al.

(10) Patent No.: US 7,241,914 B2
(45) Date of Patent: Jul. 10, 2007

(54) METHOD FOR PRODUCING POLYESTERPOLYOLS OF POLYVALENT ALCOHOLS

(75) Inventors: Alexander Wartini, Heidelberg (DE); Matthias Dernbach, Dossenheim (DE); Gerlinde Tischer, Ruhland (DE); Tilman Sirch, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/512,851

(22) PCT Filed: May 21, 2003

(86) PCT No.: PCT/EP03/05307

§ 371 (c)(1),
(2), (4) Date: Nov. 12, 2004

(87) PCT Pub. No.: WO03/099902

PCT Pub. Date: Dec. 4, 2003

(65) Prior Publication Data

US 2005/0203268 A1    Sep. 15, 2005

(30) Foreign Application Priority Data

May 24, 2002  (DE) ............................... 102 23 055

(51) Int. Cl.
*C07C 69/34* (2006.01)
(52) U.S. Cl. ..................................... 560/198
(58) Field of Classification Search ...................... None
See application file for complete search history.

(56) References Cited

U.S. PATENT DOCUMENTS

| | | |
|---|---|---|
| 3,097,245 A | 7/1963 | Ruhf et al. |
| 4,076,665 A | 2/1978 | Lawson |
| 5,525,683 A | 6/1996 | Akdins et al. |
| 6,018,074 A | 1/2000 | Kratz et al. |
| 6,096,905 A | 8/2000 | Supplee et al. |
| 6,187,971 B1 | 2/2001 | Kratz et al. |
| 2002/0189926 A1* | 12/2002 | Dernbach et al. .............. 203/14 |

FOREIGN PATENT DOCUMENTS

| | | |
|---|---|---|
| DE | 100 29 055 | 1/2002 |
| EP | 0 338 540 | 10/1989 |
| EP | 0 807 617 | 11/1997 |
| EP | 0 908 481 | 4/1999 |
| EP | 0 970 995 | 1/2000 |
| GB | 1 218 509 | 1/1971 |
| GB | 1 290 036 | 9/1972 |
| WO | 97/16401 | 5/1997 |
| WO | 01/47847 | 7/2001 |

\* cited by examiner

*Primary Examiner*—Paul A. Zucker
(74) *Attorney, Agent, or Firm*—Oblon, Spivak, McClelland, Maier & Neustadt, P.C.

(57) ABSTRACT

The invention provides a process for preparing polyester polyols of polyhydric alcohols by mono- or polyesterification of at least one carboxylic acid having at least two acid groups and/or at least one derivative of a dicarboxylic acid with polyhydric alcohols, optionally with the addition of a catalyst, while removing the water of reaction, wherein the polyhydric alcohol used has a formaldehyde acetal content of less than 500 ppm.

14 Claims, No Drawings

METHOD FOR PRODUCING POLYESTERPOLYOLS OF POLYVALENT ALCOHOLS

CROSS REFERENCES TO RELATED APPLICATIONS

This application is a national stage application of International Patent Application No. PCT/EP03/05307, filed on May 21, 2003, and claims priority to German Patent Application No. 102 23 055.2, filed on May 24, 2002, both of which are incorporated herein by reference in their entireties.

BACKGROUND OF THE INVENTION

1. Field of the Invention

The present invention describes a process for preparing polyester polyols of polyhydric alcohols by mono- or polyesterification of a dicarboxylic acid and/or an anhydride of a dicarboxylic acid with the corresponding polyhydric alcohols, optionally in a solvent and optionally with the addition of an acidic catalyst, while removing the water of reaction.

2. Description of the Background

Polyhydric alcohols are those compounds which have more than one hydroxyl group, for example from 2 to 6, preferably from 2 to 4, preferably 2 or 3.

Such polyester polyols serve as a precursor for polyurethanes, polyester resins and polyacrylates and are thus used in numerous applications.

These applications require in particular products which are very weakly colored, if at all, and have no inherent odor and high storage stability.

The preparation of polyester polyols from polyhydric alcohols and dicarboxylic acids with the exclusion of water is generally known.

The reactions conventionally take place with catalysis, for example with an acid, or merely by increasing the temperature, with or without vacuum treatment.

Since the polyester polyols of polyhydric alcohols generally cannot be distillatively purified owing to their high boiling points, by-products remain in the target ester and influence the further processing and/or quality both of the target ester and also of the subsequent products.

SUMMARY OF THE INVENTION

It is an object of the present invention to provide an economical process which facilitates the preparation of polyester polyols of polyhydric alcohols on an industrial scale in high purity and in high yield in a simple manner and without additional assistants.

We have found that this object is achieved by a process for preparing polyester polyols by reacting polyhydric alcohols with at least one dicarboxylic acid and/or a derivative, for example an anhydride, of a dicarboxylic acid, optionally in a solvent, while removing the water of reaction, wherein the polyhydric alcohol used has a formaldehyde acetal content of less than 500 ppm.

DETAILED DESCRIPTION OF THE PREFERRED EMBODIMENTS

The novel process has the following decisive advantage: the end product is distinctly less strongly colored, color number variations between different production campaigns do not occur and the misting or fogging of ingredients in the product can be avoided.

The polyhydric alcohols used may be, for example, trimethylolbutane, trimethylolpropane, trimethylolethane, neopentyl glycol, pentaerythritol, 2-ethyl-1,3-propanediol, 2-methyl-1,3-propanediol, glycerol, ditrimethylolpropane, dipentaerythritol, bisphenol A, bisphenol F, bisphenol B, bisphenol S, 2,2-bis(4-hydroxycyclohexyl)propane, 1,1-, 1,2-, 1,3- and 1,4-cyclohexanedimethanol, 1,2-, 1,3- or 1,4-cyclohexanediol, sorbitol, mannitol, diglycerol, erythritol or xylitol.

Preference is given to using those polyhydric alcohols in the process according to the invention which are obtained by reacting an aldehyde with formaldehyde and subsequently converting the aldehyde group to a hydroxyl group.

These include, for example, polyhydric alcohols of the formula (I):

where $R^1$, $R^2$ are each independently hydrogen, $C_1$–$C_{10}$-alkyl, $C_1$–$C_{10}$-hydroxyalkyl, carboxyl or $C_1$–$C_4$-alkoxycarbonyl, preferably hydrogen, hydroxymethyl or $C_1$–$C_{10}$-alkyl and more preferably hydroxymethyl or $C_1$–$C_{10}$-alkyl.

The alkyl radicals may each be straight-chain or branched.

Examples of $R^1$ and $R^2$ include hydrogen, methyl, ethyl, iso-propyl, n-propyl, n-butyl, isobutyl, sec-butyl, tert-butyl, n-pentyl, n-hexyl, n-heptyl, n-octyl, n-decyl, hydroxymethyl, carboxyl, methoxycarbonyl, ethoxycarbonyl or n-butoxycarbonyl, and preference is given to hydrogen, hydroxymethyl, methyl and ethyl, particular preference to hydroxymethyl, methyl and ethyl.

Examples of polyhydric alcohols of the formula (I) include trimethylolbutane, trimethylolpropane, trimethylolethane, neopentyl glycol, pentaerythritol, 2-ethyl-1,3-propanediol, 2-methyl-1,3-propanediol, 1,3-propanediol, dimethylolpropionic acid, methyl dimethylolpropionate, ethyl dimethylolpropionate, dimethylolbutyric acid, methyl dimethylolbutyrate or ethyl dimethylolbutyrate, and preference is given to neopentyl glycol, trimethylolpropane, pentaerythritol and dimethylolpropionic acid, particular preference to neopentyl glycol, trimethylolpropane and pentaerythritol, very particular preference to trimethylolpropane and pentaerythritol and in particular to trimethylolpropane.

Such polyhydric alcohols of the formula (I) are obtainable, for example, by reacting an aldehyde of the formula (II)

where $R^1$ and $R^2$ are each as defined above with formaldehyde and subsequently converting the aldehyde group to a hydroxyl group.

To prepare the polyester polyols according to the invention, the acids used may be carboxylic acids having at least two acid groups, preferably aliphatic or aromatic dicarboxylic acids, in particular those having from 2 to 12 carbon atoms. Examples of useful dicarboxylic acids include: adipic acid, succinic acid, glutaric acid, suberic acid, azelaic acid, sebacic acid, decanedicarboxylic acid, maleic acid, fumaric acid, dimeric and/or trimeric fatty acids, and preferably adipic acid, phthalic acid, isophthalic acid, terephthalic acid and the isomeric naphthalenedicarboxylic acids. The dicarboxylic acids may be used either individually or as a mixture with one another. Instead of the free dicarboxylic acids, the corresponding dicarboxylic acid derivatives, for example dicarboxylic esters of alcohols having from 1 to 4 carbon atoms or dicarboxylic anhydrides, may also be used. Preference is given to using dicarboxylic acid mixtures of succinic, glutaric and adipic acid in ratios of, for example, from 20 to 35:from 35 to 50:from 20 to 32 parts by weight and adipic acid and in particular mixtures of phthalic acid and/or phthalic anhydride and adipic acid, mixtures of phthalic acid/anhydride, isophthalic acid and adipic acid, or dicarboxylic acid mixtures of succinic, glutaric and adipic acid, and mixtures of terephthalic acid and adipic acid, or dicarboxylic acid mixtures of succinic, glutaric and adipic acid. For use in rigid polyurethane foams, preference is given to using aromatic carboxylic acids or mixtures which comprise aromatic carboxylic acids. Preference is further given to concomitantly using fatty acids and their derivatives, and also dimeric and/or trimeric fatty acids individually or in a mixture. Polyester alcohols based on long-chain carboxylic acids, in particular fatty acids, may be used with preference for preparing alkyd resins which may be further processed to coatings.

The alcohols of the general formula (I) may be used in a mixture with further polyhydric alcohols, preferably diols, having from 2 to 12 carbon atoms, preferably from 2 to 6 carbon atoms. Examples of di- and polyhydric alcohols, in particular diols, include: ethanediol, diethylene glycol, 1,2- and 1,3-propanediol, dipropylene glycol, 1,4-butanediol, 1,5-pentanediol, 1,6-hexanediol, 1,10-decanediol, glycerol and trimethylolpropane. Preference is given to using ethanediol, diethylene glycol, 1,4-butanediol, 1,5-pentanediol, 1,6-hexanediol or mixtures of at least two of the diols mentioned, in particular mixtures of 1,4-butanediol, 1,5-pentanediol and 1,6-hexanediol. It is also possible to use polyester polyols of lactones, for example ε-caprolactone or hydroxycarboxylic acids, for example ω-hydroxycaproic acid and hydroxybenzoic acids.

If desired, monofunctional alcohols and/or carboxylic acids may be used in a mixture with the polyfunctional alcohols and carboxylic acids to adjust the functionality. Examples of monofunctional carboxylic acids include monomeric fatty acids, for example oleic acid or ricinoleic acid. Examples of monomeric alcohols include aliphatic alcohols having from to 1 to 15, preferably from 2 to 10, carbon atoms, for example hexanol, octanol, nonanol or decanol.

Preference is given to using the alcohols of the general formula (I), in particular when they have a functionality of greater than 2, in a maximum amount of 50% by weight, based on the weight of the polyester alcohol, since undesired crosslinking otherwise occurs, accompanied by a high viscosity of the polyester alcohols.

To prepare the polyester polyols, the organic, for example aliphatic and preferably aromatic, carboxylic acids, and mixtures of aromatic and aliphatic polycarboxylic acids and/or derivatives and polyhydric alcohols can be polycondensed in the absence of a catalyst or preferably in the presence of esterification catalysts, advantageously in an atmosphere of inert gases, for example, nitrogen, carbon monoxide, helium, argon, etc., in the melt at temperatures of from 150 to 250° C., preferably from 180 to 220° C., optionally under reduced pressure, up to the desired acid number which is advantageously less than 10, preferably less than 2. To prepare the polyester polyols, the organic polycarboxylic acids and/or derivatives and polyhydric alcohols are advantageously polycondensed in a molar ratio of from 1:1 to 1.8, preferably from 1:1.05 to 1.2.

The catalysts used may be acidic catalysts such as toluenesulfonic acids, preferably organometallic compounds, in particular those based on titanium or tin, such as titanium tetrabutoxide or tin (II) octanoate.

It is also posible to react the polyhydric alcohol initially with alkylene oxides to give a polyether alcohol and then to esterify this with carboxylic acids. It is equally possible to add an alkoxylation catalyst to the polyester alcohol prepared according to the process of the invention to add on alkylene oxide. The polyether esterols obtained in this manner are notable for good compatibility with polyetherols and polyesterols and may be used with preference for preparing polyurethanes.

The polyhydric alcohols (I) are obtained on an industrial scale by condensation of formaldehyde with higher, CH-acidic aldehydes (II) or with water and acrolein or 2-alkylacroleins. In this reaction, a distinction is drawn between two principal variants of carrying out the conversion of the aldehyde group to a hydroxyl group which are illustrated hereinbelow by the preparation of trimethylolpropane but are in no way limited thereto.

Firstly, there is the Cannizzaro process which is in turn divided into the inorganic and the organic Cannizzaro processes. In the inorganic variant, an excess of formaldehyde is reacted with the appropriate aldehyde (II), i.e. n-butyraldehyde, in the presence of stoichiometric amounts of an inorganic base such as NaOH or Ca(OH)$_2$. The dimethylolbutanal formed in the first stage reacts in the second stage with the excess formaldehyde in a disproportionation reaction to give trimethylolpropane and the formate of the base used, i.e. sodium formate or calcium formate. The occurrence of these salts is a disadvantage, since they are difficult to remove from the reaction product and in addition an equivalent of formaldehyde is lost.

In the organic Cannizzaro process, a tertiary alkylamine is used instead of an inorganic base. This allows higher yields to be achieved than when using an inorganic base. Trialkylammonium formate is obtained as an undesired by-product. One equivalent of formaldehyde is accordingly likewise lost.

The disadvantages of the Cannizzaro process are avoided by the hydrogenation process. This involves reacting formaldehyde with the appropriate aldehyde (II) in the presence of catalytic amounts of an amine. This achieves the stopping of the reaction substantially at the stage of the alkylolated aldehyde. After removing the formaldehyde, the reaction mixture which, as well as the alkylolated aldehyde mentioned, still comprises small amounts of the appropriate polyhydric alcohol and of acetals of the alcohols formed is subjected to a catalytic hydrogenation to obtain the desired polyhydric alcohol.

A particular effective process for preparing polyhydric alcohols obtainable by condensation of aldehydes with formaldehyde is described in WO 98/28253. High yields combined with the occurrence of only small amounts of coupling products are facilitated by this process. The procedure is to react the higher aldehyde with the from 2- to 8-fold amount of formaldehyde in the presence of a tertiary amine and to separate the reaction mixture obtained in this manner into two solutions, one of which contains a completely methylolated alkanal mentioned and the other unconverted starting product. The latter solution is recycled into the reaction. The separation is effected by distillation or simple removal of the aqueous from the organic phase. The solution containing the product is subjected to a catalytic and/or thermal treatment in order to convert incompletely alkylolated alkanals to the desired fully methylolated compounds. Any by-product formed is removed by distillation and the liquid phase obtained in this manner is subjected to catalytic hydrogenation which leads to the polyhydric alcohols.

In the process according to the invention for preparing polyester polyols, particular preference is given to using polyhydric alcohols of the formula (I) which have been obtained by the hydrogenation process, i.e. by reacting an aldehyde of the formula (II) with formaldehyde and subsequently converting the aldehyde group to a hydroxyl group by catalytic hydrogenation, more preferably those which have been obtained by the process described in WO 98/28253.

It is essential to the invention that the formaldehyde acetal content in the polyhydric alcohol used be less than 500 ppm by weight and preferably less than 400 ppm by weight.

The formaldehyde acetals (formals) are those cyclic or aliphatic compounds which comprise the structural element

$$\text{—O—CH}_2\text{—O—} \quad \text{(formula III)}$$

These may be either hemiacetals or full acetals which are derived from main components and impurities, or else from by-products, intermediates or subsequent products of the reaction mixture.

These may be, for example, the following formaldehyde acetals of the formula (IV):

(IV)

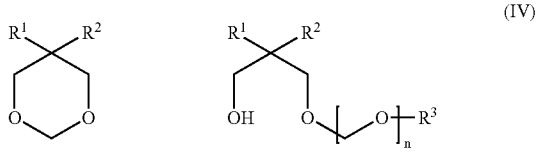

where $R^1$ and $R^2$ are each as defined above, and in addition $R^3$ is straight-chain or branched $C_1$–$C_{10}$-, preferably $C_1$–$C_8$- and more preferably $C_1$–$C_5$-alkyl, straight-chain or branched $C_1$–$C_{10}$-, preferably $C_1$–$C_8$- and more preferably $C_1$–$C_6$-hydroxyalkyl or hydrogen and n is an integer from 1 to 4, preferably from 1 to 3 and more preferably 1 or 2.

Examples of $R^3$ include hydrogen, methyl, ethyl, n-propyl, n-butyl, 2-methylpropyl, 2-methylbutyl, 2-ethyl-3-hydroxypropyl, 2-methyl-3-hydroxypropyl, 2,2-bis(hydroxymethyl)butyl, 2,2-bis(hydroxymethyl)propyl, 2,2-dimethyl-3-hydroxypropyl, 3-hydroxypropyl, 3-hydroxy-2-(hydroxymethyl)propyl or 3-hydroxy-2,2-bis(hydroxymethyl)propyl.

The formaldehyde acetals are preferably the following:

(IVa)

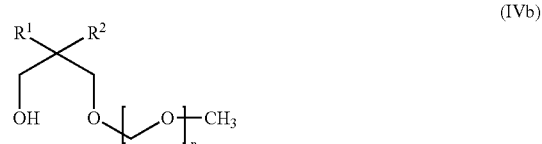

(IVb)

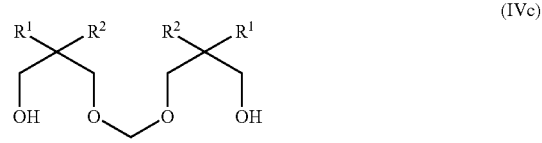

(IVc)

where $R^1$, $R^2$ and n are each as defined above.

The formaldehyde acetals are more preferably IVa, IVb (n=1), IVb (n=2) and IVc.

The methanol acetals are formed from methanol which is generally present in formaldehyde at a low level, or is formed in small amounts during the preparation by a Cannizzaro reaction of formaldehyde.

In the case of the synthesis of the trihydric alcohol trimethylolpropane (TMP) from formaldehyde and n-butyraldehyde in the presence of catalytic amounts of trialkylamine, for example, typical formaldehyde acetals are IVa, IVb (n=1), IVb (n=2) and IVc where each $R^1$ is ethyl and each $R^2$ is hydroxymethyl, each of which may be present in the crude product of the hydrogenation process in amounts of from 0.05 to 10% by weight.

The formaldehyde acetal content is calculated from the sum of the molar weight proportion of formaldehyde equivalents in each formaldehyde acetal multiplied by its analytically determined weight fraction in the reaction mixture.

For instance, the formaldehyde acetal content for a trimethylolpropane mixture ($R^1$=ethyl, $R^2$=hydroxymethyl) which comprises the components (IVa), (IVb, where n=1 and n=2) and also (IVc), for example, is calculated as follows:

$$\begin{aligned}
\text{formaldehyde acetal content} \\ \text{[\% by weight]} \end{aligned} = \text{\% by weight of (IVa)} \times \frac{30 \text{ g/mol}}{146 \text{ g/mol}} + $$

$$\text{\% by weight of (IVb, } n=1) \times \frac{30 \text{ g/mol}}{178 \text{ g/mol}} +$$

$$\text{\% by weight of (IVb, } n=2) \times \frac{2 \times 30 \text{ g/mol}}{208 \text{ g/mol}} +$$

$$\text{\% by weight of (IVc)} \times \frac{30 \text{ g/mol}}{280 \text{ g/mol}}$$

In order to obtain the corresponding formaldehyde acetal content in ppm by weight, this value has to be multiplied by 10 000.

The content of each component can be determined by those skilled in the art by analytical methods known per se, for example by gas chromatography or HPLC. For example, it is possible to identify each component by coupling the analytical methods mentioned with mass spectrometry.

It is irrelevant to the invention how such a low formaldehyde acetal content in the polyhydric alcohol is achieved.

U.S. Pat. No. 6,096,905 discloses a process by which a composition comprising formaldehyde acetals is treated with a strongly acidic catalyst at from 30 to 300° C. for ½ to 8 hours.

GB-A 1 290 036 describes a process by which a crude TMP solution obtained by the inorganic Cannizzaro process is treated with a cation exchanger.

A preferred process by which the formaldehyde acetal content in a polyhydric alcohol can be reduced consists in purifying the polyhydric alcohol after its preparation by distillation, then subjecting it to heat treatment and then purifying it again, preferably by distillation, as described in the German application having the reference number 100 29 055.8 and the application date Jun. 13, 2000 from BASF AG or in the international application having the title "Removal of formaldehydic acetals from polyhydric alcohols by heat treatment" of BASF AG.

When polyhydric alcohols are used in such a heat treatment step, particularly good results can be achieved when using alcohol solutions having a content of more than 60%, preferably >75%, more preferably >90%, even more preferably >95% and in particular >98%. Examples of further components of the alcohol solutions may include solvents, for example water, methanol, ethanol or n-butanol, and also by-products occurring in the preparation of the polyhydric alcohol, preferably in amounts of less than 10% by weight, more preferably in amounts of less than 5% by weight and most preferably of less than 2% by weight.

This process may be used to reduce the formaldehyde acetal content in polyhydric alcohols, preferably those alcohols of the formula (I) and in particular trimethylolpropane of any origin. Charges may be used which result from the organic or the inorganic Cannizzaro process. The best results were obtained when alcohols which stem from the hydrogenation process were used in the process serving to reduce the formaldehyde acetal. In any case, it is important that the alcohol has been previously purified and has a purity in the abovementioned range.

When the process is to be used to remove formaldehyde acetals from crude solutions of polyhydric alcohols, in particular of trimethylolpropane, having product contents of from 60 to 95% by weight, preference is given to subjecting the crude product obtained after the hydrogenation process (hydrogenation effluent) before the heat treatment step to dewatering in which the water and other low boilers such as methanol and trialkylamine or trialkylammonium formate are removed by distillation.

In order to achieve the desired reduction in the formaldehyde acetal content in this process, certain reaction conditions have to be maintained which may vary depending, for instance, on the type of polyhydric alcohol used, the purity of the products used, the apparatus used and any further components or additives present. These reaction conditions may be obtained by those skilled in the art by experiments.

In general, the heat treatment step is carried out at temperatures of from 100 to 300° C., preferably from 160 to 240° C., at residence times of from 5 min to 24 h, preferably from 15 min to 4 h and at pressures from 100 mbar to 200 bar, preferably from 1 to 10 bar.

When the polyhydric alcohol to be purified is trimethylopropane, the heat treatment step is carried out at temperatures from 100 to 300° C., preferably from 160 to 240° C., residence times of 10 mm to 24 h, preferably from 1 h to 5 h, more preferably from 30 min to 6 h and most preferably from 45 min to 4 h, and at the abovementioned pressures.

To carry out the heat treatment step, the customary apparatus known to those skilled in the art may be used continuously or batchwise. In batchwise operation, preference is given to carrying out the heat treatment step in a stirred vessel, and in the batchwise procedure in a tubular reactor employing either the liquid phase or trickle method.

The most preferred embodiment of the heat treatment step is the continuous operation in a tubular reactor in the liquid phase method.

In all these operation variants, the reaction vessel may be provided with the customary dense packings known to those skilled in the art, for example Raschig or Pall rings, or with structured packings, for example sheet metal packings, in order to achieve better mixing of the components. Supports and/or catalysts may also be present in the customary forms, for example extrudates or tablets, in order to accelerate the reactions proceeding in the heat treatment step. Examples of suitable supports/catalysts include $TiO_2$, $Al_2O_3$, $SiO_2$, supported phosphoric acid ($H_3PO_4$) and zeolites.

In one variant of the heat treatment step, a suitable additive is added to the reaction solution during the heat treatment step in order to accelerate and ease the reactions leading to the reduction in the amounts of formaldehyde acetals. Examples thereof include not too strong and/or reducing acids or their anhydrides or ion exchangers, as described in U.S. Pat. No. 6,096,905 or GB 1 290 036. Examples of suitable acids include phosphoric acid, phosphorous acid, hypophosphorous acid, boric acid, carbonic acid and sulfurous acid. Gases, for example $CO_2$ and $SO_2$, which react acidically in aqueous solution, are also suitable.

The acids to be used as additives are used in amounts of from 10 ppm to 1% by weight, preferably from 100 to 2000 ppm. Since the additive possibly added has to be removed from the formaldehyde acetal-reduced polyhydric alcohol after the heat treatment step, preference is given to this additive being gaseous and accordingly being easy to remove from the reaction mixture by outgassing.

It may further be advantageous to carry out the heat treatment step for decomposing the formaldehyde acetals under an inert gas, for example nitrogen, argon or helium, preferably under nitrogen.

Without wishing to be bound to a theory, it is suspected that formaldehyde acetals are converted by the heat treatment step in the alcohol prepurified by distillation into higher-boiling, involatile and low-boiling components and can thus be distillatively removed more easily.

The polyhydric alcohol having a reduced formaldehyde acetal content can be easily removed from the high-boiling involatile components formed by distillation. The heat treatment step is therefore generally followed by a distillation. Since the involatile components formed from the formaldehyde acetals in the heat treatment step generally differ markedly from the polyhydric alcohols with regard to their boiling behavior, these may be removed by simple distinctive measures or methods having only a small separating effect. Separating units having only one distillation stage, for example falling-film evaporators or thin-film evaporators, often suffice. Particularly when the distillation also serves for further purification of the product alcohol, more complicated separating processes or separating apparatus may optionally be used, generally columns having more than one separating stage, for example randomly packed columns, bubble cap tray columns or columns having structured packing.

The distillation is carried out using the customary conditions with regard to pressure and temperature known to those skilled in the art, although it will be appreciated that these also depend on the product alcohol used.

According to a further embodiment, the heat treatment step may also be combined with the distillation. In this embodiment, the heat treatment takes place in the column bottom of the distillation apparatus in which the polyhydric product alcohol is removed from involatile components formed in the heat treatment and also any other impurities. When the heat treatment step and distillation are combined in one stage, it is important that the above-specified reaction conditions with regard to pressure, temperature and in particular residence time are maintained in order to achieve sufficient decomposition of the formaldehyde acetals. When the heat treatment and distillation steps are combined in a single process step, preference is given to adding acid.

The polyhydric alcohol obtainable by this process generally has a formaldehyde acetal content as defined above of less than 500 ppm by weight, preferably less than 400 ppm by weight.

It is unimportant by which process the polyhydric alcohol has been obtained, for example by the Cannizzaro or by the hydrogenation process.

The polyesterols prepared by the process according to the invention may be reacted with, for example, polyisocyanates to give polyurethanes.

Unless otherwise stated, ppm and percentage data used in this document refer to percent by weight and ppm by weight.

EXAMPLES

Preparation of polyester polyols for industrial rigid foam:

Example I

In a laboratory stirred apparatus equipped with heating, a nitrogen bubbler, a randomly packed column and distillation apparatus, 204.1 g of oleic acid, 105.6 g of adipic acid, 214.1 g of phthalic anhydride and 541.2 g of TMP (formaldehyde acetal content 280 ppm, diformalin and methanol content 0.4%) were initially charged and heated to 170° C. with stirring. After removing 60.4 g of water of reaction, the temperature was increased to 220° C. While continuing to remove the distillate formed, the reaction was conducted up to an acid number of less than 0.5 mg of KOH/g.

Example II and III (comparison)

In accordance with example I, the synthesis was repeated using TMP having a formaldehyde acetal content of 620 ppm and 1 400 ppm.

| Experiment No. | Formaldehyde acetal content of the TMP used [ppm by weight] | Color number of the polyester polyol [iodine color number] |
|---|---|---|
| I | 280 | 7.5 |
| II | 620 | 8.1 |
| III | 1400 | 8.6 |

We claim:
1. A process for preparing a polyester polyol of a polyhydric alcohol, comprising:
    mono- or polyesterifying at least one carboxylic acid having at least two acid groups, at least one derivative of a dicarboxylic acid or a combination thereof with a polyhydric alcohol, optionally in the presence of a catalyst, while removing the water of reaction, wherein the polyhydric alcohol contains formaldehyde acetals, wherein the formaldehyde acetals are present in a reduced amount of less than 500 ppm, and
    wherein the polyester polyol has a lower iodine color number than a corresponding polyester polyol containing formaldehyde acetals in amounts greater than 500 ppm.
2. The process as claimed in claim 1, wherein the polyhydric alcohol is an alcohol of the formula (I)

where $R^1$ and $R^2$ are each independently hydrogen, $C_1$–$C_{10}$-alkyl, $C_1$–$C_{10}$-hydroxyalkyl, carboxyl or $C_1$–$C_4$-alkoxycarbonyl.
3. The process as claimed in claim 1, wherein the polyhydric alcohol is trimethylolbutane, trimethylolpropane, trimethylolethane, neopentyl glycol, pentaerythritol, 2-ethyl-1,3-propanediol, 2-methyl-1,3-propanediol or 1,3-propanediol.
4. The process as claimed in claim 1, wherein the polyhydric alcohol is purified by distillation, then subjected to heat treatment and then purified again.
5. The process as claimed in claim 4, wherein the heat treatment is carried out at a temperature ranging from 100 to 300° C.
6. The process as claimed in claim 1, wherein the carboxylic acids having at least two acid groups are aliphatic or aromatic dicarboxylic acids having from 2 to 12 carbon atoms.
7. The process as claimed in claim 1, wherein one or more monofunctional carboxylic acids are used in a mixture with the carboxylic acids having at least two acid groups.
8. The process as claimed in claim 7, wherein oleic acid is used as a monofunctional carboxylic acid.
9. The process as claimed in claim 2, wherein the polyhydric alcohol of formula (I) is prepared by reacting an aldehyde of formula (II):

wherein $R^1$ and $R^2$ are each as defined above, with formaldehyde, followed by reduction of the product of the reaction to the polyhydric alcohol.
10. The process as claimed in claim 1, wherein the polyhydric alcohol consists of one or more polyhydric alcohols selected from the group consisting of trimethylolbutane, trimethylolpropane, trimethylolethane, neopentyl glycol, pentaerythritol, 2-ethyl-1,3-propanediol, 2-methyl-1,3-propanediol, glycerol, ditrimethylolpropane, dipentaerythritol, bisphenol A, bisphenol F, bisphenol B, bisphenol S, 2,2-bis(4-hydroxycyclohex)propane, 1,1-, 1,2-, 1,3- and 1,4-cyclohexanedimethanol, 1,2-, 1,3- and 1,4-cyclohexanediol, sorbitol, mannitol, diglycerol, erythritol, xylitol, 1,3-propanediol, dimethylolpropionic acid, methyl dimethylolpropionate, ethyl dimethylolpropionate, dimethylolbutyric acid, methyl dimethylolbutyrate, ethyl dimethylolbutyrate, ethanediol, diethylene glycol, 1,2- and 1,3-propanediol, dipropylene glycol, 1,4-butanediol, 1,5-pentanediol, 1,6-hexanediol, 1,10-decanediol, and glycerol.

11. The process as claimed in claim 1, wherein the polyhydric alcohol consists of at least one of trimethylolpropane and pentaerythritol.

12. The process as claimed in claim 1, wherein the polyhydric alcohol consists of trimethylolpropane.

13. The process as claimed in claim 1, wherein the formaldehyde acetal amount is less than 400 ppm.

14. The process as claimed in claim 1, wherein the polyester polyol contains alkylene oxide groups, which groups have been introduced either by reacting the polyhydric alcohol with an alkylene oxide prior to said polyesterifying or by reacting said polyester polyol after preparation thereof with an alkylene oxide.

* * * * *